(12) United States Patent
Farcet

(10) Patent No.: US 10,117,824 B2
(45) Date of Patent: *Nov. 6, 2018

(54) GRADIENT COPOLYMER, COMPOSITION INCLUDING SAME AND COSMETIC MAKE-UP OR CARE METHOD

(71) Applicant: L'OREAL, Paris (FR)

(72) Inventor: Celine Farcet, Paris (FR)

(73) Assignee: L'OREAL, Paris (FR)

( * ) Notice: Subject to any disclaimer, the term of this patent is extended or adjusted under 35 U.S.C. 154(b) by 394 days.

This patent is subject to a terminal disclaimer.

(21) Appl. No.: 14/255,103

(22) Filed: Apr. 17, 2014

(65) Prior Publication Data
US 2014/0227210 A1 Aug. 14, 2014

Related U.S. Application Data

(62) Division of application No. 11/628,954, filed as application No. PCT/FR2005/001445 on Jun. 10, 2005, now Pat. No. 9,827,183.

(60) Provisional application No. 60/586,313, filed on Jul. 9, 2004.

(30) Foreign Application Priority Data

Jun. 11, 2004 (FR) ...................... 04 06369

(51) Int. Cl.
| | | |
|---|---|---|
| A61K 8/81 | (2006.01) | |
| A61Q 1/02 | (2006.01) | |
| A61Q 1/06 | (2006.01) | |
| A61Q 3/02 | (2006.01) | |
| C08F 220/14 | (2006.01) | |
| C08F 220/18 | (2006.01) | |
| A61Q 1/10 | (2006.01) | |
| A61Q 5/02 | (2006.01) | |
| A61Q 5/06 | (2006.01) | |
| A61Q 17/04 | (2006.01) | |
| A61Q 19/00 | (2006.01) | |

(52) U.S. Cl.
CPC .............. *A61K 8/8152* (2013.01); *A61Q 1/02* (2013.01); *A61Q 1/06* (2013.01); *A61Q 3/02* (2013.01); *C08F 220/14* (2013.01); *C08F 220/18* (2013.01); *A61K 2800/54* (2013.01); *A61Q 1/10* (2013.01); *A61Q 5/02* (2013.01); *A61Q 5/06* (2013.01); *A61Q 17/04* (2013.01); *A61Q 19/00* (2013.01)

(58) Field of Classification Search
CPC combination set(s) only.
See application file for complete search history.

(56) References Cited

U.S. PATENT DOCUMENTS

| | | |
|---|---|---|
| 5,625,005 A | 4/1997 | Mallya et al. |
| 5,919,871 A | 7/1999 | Nicol et al. |
| 6,153,705 A | 11/2000 | Corpart et al. |
| 6,255,448 B1 | 7/2001 | Grimaldi et al. |
| 6,262,179 B1 | 7/2001 | Nicol |
| 6,294,158 B1 * | 9/2001 | Dupuis ..................... 424/70.1 |
| 6,403,106 B1 | 6/2002 | Sebag et al. |
| 6,407,158 B1 | 6/2002 | Kim et al. |
| 6,545,098 B1 | 4/2003 | Bouhadir et al. |
| 6,657,043 B1 | 12/2003 | Guerret et al. |
| 6,689,346 B1 | 2/2004 | Rollat et al. |
| 6,812,291 B1 | 11/2004 | Corpart et al. |
| 7,345,121 B2 | 3/2008 | Suau et al. |
| 2003/0096929 A1 | 5/2003 | Olson et al. |
| 2003/0208012 A1 | 11/2003 | Mathew et al. |
| 2004/0054108 A1 | 3/2004 | Mestach et al. |
| 2004/0185017 A1 | 9/2004 | Mougin et al. |
| 2004/0191199 A1 | 9/2004 | Mougin |
| 2004/0202688 A1 | 10/2004 | Mougin et al. |
| 2005/0255068 A9 | 11/2005 | Mougin |

FOREIGN PATENT DOCUMENTS

| | | |
|---|---|---|
| EP | 0096459 A2 | 12/1983 |
| EP | 0895467 A1 | 2/1999 |
| EP | 1428493 A1 | 6/2004 |
| EP | 1428495 A1 | 6/2004 |
| EP | 1428496 A1 | 6/2004 |
| FR | 2821620 A1 | 9/2002 |
| JP | 2000302837 A | 10/2000 |
| JP | 2002193768 A | 7/2002 |
| JP | 2004196802 A | 7/2004 |
| WO | WO-9624620 A1 | 8/1996 |
| WO | WO-96/30421 A1 | 10/1996 |
| WO | WO-9801478 A1 | 1/1998 |
| WO | WO-9858974 A1 | 12/1998 |
| WO | WO-9931144 A1 | 6/1999 |
| WO | WO-9935177 A1 | 7/1999 |
| WO | WO-0071501 A1 | 11/2000 |

OTHER PUBLICATIONS

Aksimentiew, A. et al., "Phase behavior of gradient copolymers," J. of Chem. Physics, 111(5):2329-2339 (1999).
Benoit, D. et al., "Development of a Universal Alkoxyamine for 'Living' Free Radical Polymerizations," J. Am. Chem. Soc., 121:3904-3920 (1999).
Benoit, D et al., "Kinetics and Mechanism of Controlled Free-Radical Polymerization of Styrene and η-Butyl Acrylate in the Presence of an Acrylic β-Phosphonylated Nitroxide," J. Am Chem. Soc. 122:5929-5939 (2000).
Brandrup, J. et al., Polymer Handbook (3rd Ed., 1989, John Wiley).
Chiefari, J. et al., "Living Free-Radical polymerization by Reversible Addition-Fragmentation Chain Transfer: The RAFT Process," Macromolecules, 31:5559-5562 (1998).
Degoulet, C. et al., "Self-Focusing in Gradient Liquid Adsorption Chromatography of Polymers," Macromolecules, 34: 2667-2672 (2001).

(Continued)

*Primary Examiner* — Hasan S Ahmed
(74) *Attorney, Agent, or Firm* — Polsinelli PC

(57) ABSTRACT

Novel gradient copolymers including at least two different and specifically selected monomers, and cosmetic or skincare compositions including same. The invention also relates to a cosmetic method for make-up or the care of keratin materials, in particular the skin of the body or of the face, the nails, the hair and/or the eyelashes, comprising the application of a cosmetic composition as defined above on said materials.

36 Claims, No Drawings

(56) References Cited

OTHER PUBLICATIONS

Fischer, H., "The Persistent Radical Effect: A Principle for Selective Radical Reactions and Living Radical Polymerizations," Chemical Review, 101:3581-3610 (2001).

Gray, M. et al., "Gradient Copolymerization of Styrene and 4-Acetoxystyrene via Nitroxide-Mediated Controlled Radical Polymerization," Polym. Prepr. (Am. Chem. Soc., Div. Polym. Chem.) 42(2):337-338 (2001).

Grukle, E.A., "Solubility Parameter Values," Polymer Handbook, 3rd Edition, Chapter VII, pp. 519-559 (1989).

Hansen, C.M., "The Three-Dimensional Solubility Parameter—Key to Paint Component Affinities: I. Solvents, Plasticizers, Polymers, and Resins," J. Paint Technol. 39(105): 104-117 (1967).

Janco, M. et al., "Rapid Determination of Molecular Parameters of Synthetic Polymers by Precipitation/Redissolution High-Performance Liquid Chromatography Using 'Molded' Monolithic Column," J. Polym. Sci., Part A: Polym. Chem., 38(15): 2767-2778 (2000).

Matyjaszewski, K. et al., "Atom Transfer Radical Polymerization," Chem. Rev., (Washington, D.C.) 101(9): 2921-2900 (2001).

Matyjaszewski, K., et al., "Gradient copolymers by atom transfer radical copolymerization," J. Phys. Org. Chem., 13:775-586 (2000).

Pakula, T. et al., "Copolymers with controlled distribution of comonomers along the chain, 1," Macromol. Theory Simul. 5:987-1006 (1996).

Zaremski, M. et al., "A Concept for Quasiliving Nitroxide-Mediated Radical Copolymerization," Macromolecules, 33(12): 4365-4372 (2000).

International Search Report for PCT/FR2005/001445, dated Dec. 9, 2005.

\* cited by examiner

GRADIENT COPOLYMER, COMPOSITION INCLUDING SAME AND COSMETIC MAKE-UP OR CARE METHOD

This application is a divisional of U.S. application Ser. No. 11/628,954 filed on Sep. 22, 2009; and this application claims priority to Application No. 0406369 filed in France on Jun. 11, 2004, and this application claims the benefit of U.S. Provisional Application No. 60/586,313 filed on Jul. 9, 2004; the entire contents of all are hereby incorporated by reference.

The present invention relates to novel topical cosmetic or dermatological compositions comprising specific gradient copolymers which are preferably soluble in the solvent medium of the composition, which can comprise cosmetic oils and/or solvents; the invention also relates to the specific copolymers.

In the field of cosmetics, there is often a search to have available compositions which make it possible to obtain a deposited layer, in particular an adhesive or film-forming deposited layer, on the keratinous substances under consideration, such as the hair, skin, eyelashes or nails.

In particular, these compositions can contribute color (make-up or hair dyeing compositions), gloss or matteness (compositions for caring for or making up the skin), physical properties, such as shaping (hair compositions, in particular styling compositions) or care or protection properties (care compositions, for example moisturizing or UV protection compositions). Good persistence and hold over time of the deposited cosmetic layer and good adhesion to the support are generally sought for. In particular, it is desirable for this deposited layer to be able to withstand mechanical attacks, such as rubbing actions or transfers by contact with another object, and to withstand water, sweat, tears, rain, sebum and oils. This is particularly true in makeup, in particular in the field of lipsticks, where prolonged hold of the color and of the gloss and the nontransfer of the color are sought for; in the field of foundations, eyeshadows and powders, where the hold of the color introduced, while maintaining the matteness of the initial makeup for as long as possible despite the secretion of sebum and sweat, and the nontransfer are sought for. In addition, the makeup compositions should be comfortable to wear and should not exhibit an excessively tacky texture.

It is possible, in order to achieve all these often conflicting properties in the same composition, to employ a blend of several polymers of very different chemical natures, each polymer contributing one of the desired characteristics. However, the use of a blend of polymers having different and not necessarily compatible chemical natures can cause problems of phase separation in the composition.

The use of random polymers, for example of conventional acrylic polymers obtained by conventional radical polymerization with a random mixture of monomers, does not make it possible to satisfactorily solve these problems. This is because the random polymers known in the prior art exhibit a dispersity in composition of the polymer chains, which also results in phase separation of the polymers in the formulation.

The aim of the present invention is to overcome the disadvantages of the prior art by providing a cosmetic or dermatological composition comprising specific polymers which prevent the problems of phase separation in the formulation while making it possible to contribute the desired cosmetic properties.

A subject matter of the present invention is thus a gradient copolymer comprising at least two different monomers both chosen from isobornyl acrylate, isobornyl methacrylate, isobutyl acrylate, isobutyl methacrylate and 2-ethylhexyl acrylate.

Another subject matter of the invention is a cosmetic or dermatological composition comprising said copolymer.

Advantageously, the copolymers according to the invention are completely soluble in the solvent medium of the composition, which can comprise cosmetic oils and/or solvents.

As the gradient copolymers according to the invention exhibit a low dispersity in composition, all the chains exhibiting virtually the same structures, they are therefore compatible with one another; the result of this is that the cosmetic compositions comprising these copolymers do not exhibit the disadvantages and limitations of the compositions of the prior art.

In particular, the copolymers according to the invention exhibit the advantage of being able to be easily employed in organic cosmetic media, in particular of oil or lipophilic solvent type, while retaining advantageous rheological properties.

The copolymers according to the invention are gradient copolymers which comprise at least two different monomers chosen from a given list and which preferably exhibit a low polydispersity in weight and preferably a low polydispersity in composition.

The polydispersity in weight can be illustrated using the weight polydispersity index (PI) of the copolymer, which is equal to the ratio of the weight-average molecular weight (Mw) to the number-average molecular weight (Mn). A low dispersity in mass reflects approximately identical chain lengths, which is the case for the copolymers according to the present invention.

Preferably, the gradient copolymer according to the invention has a weight polydispersity index of less than or equal to 3, preferably of between 1.1 and 2.5, in particular between 1.15 and 2.3, indeed even between 1.2 and 2.0, or 1.9 or even 1.8.

Furthermore, the weight-average molecular weight of the gradient copolymer is preferably between 2000 g/mol and 1 000 000 g/mol, in particular between 3000 g/mol and 800 000 g/mol and better still between 5000 g/mol and 500 000 g/mol.

Preferably, the number-average molecular weight of the gradient copolymer is between 2000 g/mol and 1 000 000 g/mol, in particular between 3000 g/mol and 800 000 g/mol and better still between 5000 g/mol and 500 000 g/mol.

The weight-average molecular weights (Mw) and the number-average molecular weights (Mn) are determined by gel permeation liquid chromatography (GPC), eluent THF, calibration curve established with linear polystyrene standards, refractometer detector.

The gradient copolymer according to the invention also preferably exhibits a low dispersity in composition. This means that all the chains of copolymers have a composition (that is to say, a sequence of monomers) which is approximately the same and are therefore homogeneous in composition. In order to show that all the chains of copolymers have a similar composition, use will advantageously be made of liquid adsorption chromatography (or LAC), which makes it possible to separate the chains of copolymers not according to their molecular weight but according to their polarity. The latter reflects the chemical composition of the polymers constituting the material, the monomers being known. Reference may be made to the publication Macromolecules (2001), 34, 2667, which describes the LAC technique.

The polydispersity in composition can be defined in particular from the adsorption chromatography (LAC) curve (curve representing the proportion of polymers as a function of the elution volume): if "$V^{1/2}$ min" is used to denote the minimum value of the elution volume at mid-height of the curve and if "$V^{1/2}$ max" is used to denote the maximum value of the elution volume at mid-height of the curve, the polydispersity in composition is generally regarded as low if the difference ($V^{1/2}$ max–$V^{1/2}$ is less than or equal to 3.5, in particular between 1 and 2.8 and better still between 1.2 and 2.5.

Furthermore, the LAC curve can be defined by a Gaussian curve of formula:

$$y = \frac{A}{w\sqrt{\frac{\pi}{2}}} \times e^{-2\frac{(x-x_0)^2}{w^2}} + y_o$$

in which:
- $x_0$ is the value of x (elution volume) at the center of the peak
- w is equal to twice the standard deviation of the Gaussian distribution (i.e. $2\sigma$) or alternatively corresponds to approximately 0.849 times the width of the peak at mid-height
- A represents the area under the peak
- $y_o$ is the value of y corresponding to $x_0$.

The dispersity in composition of the copolymer according to the invention can also be defined by the value w as defined above. Preferably, said value w is between 1 and 3, in particular between 1.1 and 2.3 and even better still between 1.1 and 2.0.

The gradient copolymers according to the invention can be obtained by living or pseudo-living polymerization. For the record, it should be remembered that living polymerization is a polymerization in which the growth of the polymer chains only stops when the monomer disappears. The number-average molecular weight (Mn) increases with the conversion. Anionic polymerization is a typical example of living polymerization. Such polymerizations result in copolymers having a low dispersity in mass, that is to say in polymers with a weight polydispersity index (PI) generally of less than 2.

For its part, pseudo-living polymerization is associated with controlled radical polymerization. Mention may be made, among the main types of controlled radical polymerization, of:
- radical polymerization controlled by nitroxides. Reference may in particular be made to patent applications WO 96/24620 and WO 00/71501, which disclose the tools of this polymerization and their use, and to the papers published by Fischer (Chemical Reviews, 2001, 101, 3581), by Tordo and Gnanou (J. Am. Chem. Soc., 2000, 122, 5929) and by Hawker (J. Am. Chem. Soc., 1999, 121, 3904);
- atom transfer radical polymerization, disclosed in particular in application WO 96/30421 and which proceeds by the reversible insertion over an organo-metallic complex in a bond of carbon-halogen type;
- radical polymerization controlled by sulfur derivatives of xanthate, dithioester, trithiocarbonate or carbamate type, such as disclosed in applications FR 2 821 620, WO 98/01478, WO 99/35177, WO 98/58974, WO 99/31144 and WO 97/01478 and in the publication by Rizzardo et al. (Macromolecules, 1998, 31, 5559).

Controlled radical polymerization denotes polymerizations in which the secondary reactions which usually result in the disappearance of propagating entities (termination or transfer reaction) are rendered highly improbable in comparison with the propagation reaction by virtue of an agent for controlling the free radicals. The disadvantage of this method of polymerization lies in the fact that, when the concentrations of free radicals become high in comparison with the concentration of monomer, the secondary reactions again become determining and tend to broaden the distribution of the weights.

By virtue of these polymerization methods, the polymer chains of the gradient copolymers according to the invention grow simultaneously and therefore incorporate at each instant the same ratio of comonomers. All the chains therefore have the same structures or similar structures, resulting in a low dispersity in composition. These chains also have a low weight polydispersity index.

Gradient copolymers are copolymers exhibiting a change in the ratio of the various monomers all along the chain. The distribution in the polymeric chains of the comonomers depends on the change during the synthesis in the relative concentrations of the comonomers.

The copolymers according to the invention comprise at least two different monomers, the concentration of which along the polymer chain changes gradually and in a systematic and predictable way.

This means that all the polymer chains have at least one monomer Mi for which, whatever the normalized position x on the polymer chain, there is a nonzero probability of encountering this monomer Mi along the chain.

One of the characteristics which makes it possible to define gradient copolymers is the fact that, at any instant in the polymerization, all the chains are subjected to the presence of the combination of all the monomers. Thus, in the reaction medium, the concentration of each monomer is always nonzero at any instant in the polymerization.

This makes it possible to distinguish the copolymers according to the invention from conventional block polymers in which the change in the monomers along the polymer chain is not systematic; for example, for an AB diblock, within the A block, the concentration of the other monomer B is always zero.

In the case of random polymers, the change in the monomers along the polymer chain will not be gradual, systematic and predictable either. A random polymer obtained by conventional radical polymerization of two monomers is distinguished from a gradient copolymer by the distribution of the monomers, which is not identical over all the chains, and by the length of said chains, which is not identical for all the chains.

For a theoretical description of gradient copolymers, reference may be made to the following publications:
T. Pakula et al., Macromol. Theory Simul., 5, 987-1006 (1996);
A. Aksimetiev et al., J. of Chem. Physics, 111, No. 5;
M. Janco, J. Polym. Sci., Part A: Polym. Chem. (2000), 38(15), 2767-2778;
M. Zaremski et al., Macromolecules (2000), 33(12), 4365-4372;
K. Matyjaszewski et al., J. Phys. Org. Chem. (2000), 13(12), 775-786;
Gray, Polym. Prepr. (Am. Chem. Soc., Div. Polym. Chem.) (2001), 42(2), 337-338;
K. Matyjaszewski, Chem. Rev. (Washington, D.C.) (2001), 101(9), 2921-2990.

Among gradient copolymers, it is possible to distinguish natural gradient copolymers and artificial gradient copolymers.

A natural gradient copolymer is a gradient copolymer synthesized as a batch from a starting mixture of the comonomers. The distribution in the chain of the various monomers follows a law deduced from the relative reactivity and from the starting concentrations of monomers. These copolymers constitute the simplest class of gradient copolymers as it is the starting mixture which defines the final product property.

An artificial gradient copolymer is a copolymer for which the concentration of monomers during the synthesis is varied by a processing expedient. In this case, a mixture of monomers is changed to another in the chain due to a sudden and abrupt change in the monomers in the reaction medium (stripping of the first mixture or addition of at least one new monomer). It is even possible for one or more of the monomers therein to completely disappear, to the advantage of one or more others.

The gradient can be characterized experimentally by measuring, during polymerization, the chemical composition of the polymer. This measurement is performed indirectly by determining the change in the content of the various monomers at any instant. It can be performed by NMR and UV spectroscopy, for example. This is because, for the polymers prepared by living or pseudo-living polymerization, the length of the chains is linearly related to the conversion. By withdrawing a sample of the polymerization solution at various instants in the polymerization and by measuring the difference in content of each monomer, the composition of the gradient is thus determined.

The distribution of the compositions of the chains is preferably narrow in the gradient polymer. In particular, there exists no overlap between the peak of the gradient copolymer and those of the respective homopolymers. This means that the material obtained under gradient conditions is composed of polymer chains with the same composition whereas, in conventional random polymerization, different kinds of chain coexist, including those of the respective homopolymers.

It is possible to characterize gradient copolymers by a vector characteristic of each copolymer. This is because, knowing that there exists an infinity of polymers characterized by a given chemical composition, to specify a polymer it is possible to describe the distribution of monomers along the chain. This involves a description comprising several variables. This vector is a point of the space of the chemical compositions. The exact term is that G is a vector, the coordinates of which are the concentrations of the monomers along the polymer chain. These concentrations are defined by the rules of the reactivity coefficients of each of the monomers and therefore are related to the concentration of the free monomers during the synthesis: from the moment that the monomer is not in zero concentration in the reaction mixture, it is not in zero concentration in the polymer.

It is therefore possible to characterize gradient copolymers by the function $G(x)$ which defines the composition gradient:

$$\vec{G}(x) = \Sigma \overrightarrow{[Mi](x)}$$

in which:
x denotes a normalized position on the polymer chain and $[Mi](x)$ is the relative concentration, in this position x, of the monomer Mi, expressed in mol %.

The function $G(x)$ therefore locally describes the composition of the gradient copolymer.

Two copolymers can have an equivalent composition overall but very different local distributions of the monomers and therefore different gradients.

For example, in the case of a (50/50) AB diblock, the function [A] has a value of 1 up to x=½, and then 0 subsequently.

The factors which determine the gradient are, first, the relative reactivity coefficients of each monomer (referred to as $r_i$ for the monomer Mi), which depend mainly on the type of synthesis process employed (homogeneous, dispersed) and on the solvents, and, secondly, the starting concentrations of each of the monomers and the possible additions of monomers during the polymerization.

The gradient copolymer according to the invention comprises at least two different monomers which are both chosen from isobornyl acrylate, isobornyl methacrylate, isobutyl acrylate, isobutyl methacrylate and 2-ethylhexyl acrylate. In the continuation of the present description, these five monomers will be referred to as "selected monomers".

The copolymer according to the invention can thus comprise from 1 to 99% by weight, with respect to the weight of the final copolymer, in particular from 2 to 98% by weight, preferably from 5 to 95% by weight, indeed even from 30 to 70% by weight, of a first monomer chosen from the "selected monomers" and from 1 to 99% by weight, with respect to the weight of the final copolymer, in particular from 2 to 98% by weight, preferably from 5 to 95% by weight, indeed even from 30 to 70% by weight, of a second monomer, different from said first monomer, chosen from the "selected monomers".

The copolymer according to the invention can also optionally comprise from 1 to 50% by weight, in particular from 5 to 40% by weight, indeed even from 10 to 35% by weight, with respect to the weight of the final copolymer, of a third monomer, different from the first and second monomers, chosen from the "selected monomers".

The total amount of monomers chosen from the selected monomers in the final copolymer is preferably between 50 and 100% by weight inclusive, in particular from 60 to 98% by weight, indeed even from 70 to 97% by weight, better still from 80 to 96% by weight, preferably from 90 to 95% by weight, with respect to the weight of the final copolymer.

Preference is very particularly given to the copolymers comprising:
  isobornyl acrylate and isobornyl methacrylate;
  isobornyl acrylate and isobutyl acrylate;
  isobornyl acrylate and isobutyl methacrylate;
  isobornyl acrylate and 2-ethylhexyl acrylate;
  isobornyl methacrylate and isobutyl acrylate;
  isobornyl methacrylate and isobutyl methacrylate;
  isobornyl methacrylate and 2-ethylhexyl acrylate;
  isobornyl acrylate, isobornyl methacrylate and 2-ethylhexyl acrylate;
  isobornyl acrylate, isobornyl methacrylate and isobutyl acrylate;
  isobornyl acrylate, isobutyl methacrylate and 2-ethylhexyl acrylate;
  isobornyl acrylate, isobutyl methacrylate and isobutyl acrylate; or
  isobornyl methacrylate, isobutyl methacrylate and isobutyl acrylate.

The copolymer according to the invention can furthermore comprise at least one additional monomer other than those chosen from the selected monomers.

This additional monomer or mixture of additional monomers can be present in an amount of 0 to 50% by weight, in particular of 2 to 40% by weight, indeed even of 3 to 30% by weight, better still of 4 to 20% by weight, preferably of 5 to 10% by weight, with respect to the weight of the final copolymer.

This or these additional monomers can be chosen, alone or as a mixture, from the following monomers and their salts, with the exception, of course, of the selected monomers mentioned above:

(i) (meth)acrylates of formula $CH_2$=CHCOOR or $CH_2$=C($CH_3$)COOR in which R represents:
  a linear or branched alkyl group comprising 1 to 30 carbon atoms in which is(are) optionally inserted one or more heteroatoms chosen from O, N, S and P and/or said alkyl group being able to be optionally substituted by one or more substituents chosen from —OH, halogen atoms (Cl, Br, I and F), —$NR_4R_5$ groups, where $R_4$ and $R_5$, which are identical or different, represent hydrogen or a linear or branched $C_1$ to $C_6$ alkyl group or a phenyl group; and/or polyoxyalkylene groups, in particular polyoxyethylene and/or polyoxy-propylene, said polyoxyalkylene group being composed of the repetition of 5 to 30 oxyalkylene units;
  a $C_3$ to $C_{12}$ cycloalkyl group, said cycloalkyl group being able to comprise, in its chain, one or more heteroatoms chosen from O, N, S and/or P and/or being able to be optionally substituted by one or more substituents chosen from —OH and halogen atoms (Cl, Br, I and F);
  a $C_4$ to $C_{20}$ aryl group or a $C_5$ to $C_{30}$ aralkyl group ($C_1$ to $C_8$ alkyl group);
  in particular, R can be a methyl, ethyl, propyl, isopropyl, n-butyl, isobutyl, tert-butyl, hexyl, ethylhexyl, octyl, lauryl, isooctyl, isodecyl, dodecyl, cyclohexyl, t-butylcyclohexyl, stearyl, 2-ethyl-perfluorohexyl, 2-hydroxyethyl, 2-hydroxybutyl, 2-hydroxypropyl, methoxyethyl, ethoxyethyl, methoxypropyl, isobornyl, phenyl, 2-phenylethyl, t-butylbenzyl, benzyl, furfurylmethyl or tetrahydrofurfuryl-methyl, methoxypolyoxyethylene (or POE-methyl), POE-behenyl, trifluoroethyl, dimethylaminoethyl, diethylaminoethyl or dimethylaminopropyl group, (ii) (meth)acrylamides of formula $CH_2$=CHCONR$_4$R$_5$ or $CH_2$=C ($CH_3$) CONR$_4$R$_5$
in which $R_4$ and $R_5$, which are identical or different, represent a hydrogen atom or:
  a) a linear or branched alkyl group comprising from 1 to 18 carbon atoms in which is(are) optionally inserted one or more heteroatoms chosen from O, N, S and P; said alkyl group being able in addition to be optionally substituted by one or more substituents chosen from hydroxyl groups, halogen atoms (Cl, Br, I and F) and Si ($R_4R_5$) groups, where $R_4$ and $R_5$, which are identical or different, represent a $C_1$ to $C_6$ alkyl group or a phenyl group;
  and in particular a methyl, ethyl, propyl, isopropyl, n-butyl, isobutyl, tert-butyl, hexyl, isohexyl, cyclohexyl, ethylhexyl, octyl, isooctyl, decyl, isodecyl, cyclodecyl, dodecyl, cyclododecyl, isononyl, lauryl, t-butylcyclohexyl, stearyl or 2-ethylperfluoro-hexyl group; or a $C_{1-4}$ hydroxyalkyl group, such as 2-hydroxyethyl, 2-hydroxybutyl and 2-hydroxypropyl; or a ($C_{1-4}$)alkoxy($C_{1-4}$)alkyl group, such as methoxyethyl, ethoxyethyl and methoxypropyl,
  b) a $C_3$ to $C_{12}$ cycloalkyl group, such as the isobornyl group, or a heterocycloalkyl group (alkyl of 1 to 4 carbon atoms), such as furfurylmethyl or tetrahydro-furfurylmethyl,
  c) a $C_4$ to $C_{20}$ aryl group, such as the phenyl group,
  d) a $C_5$ to $C_{30}$ aralkyl group ($C_1$ to $C_8$ alkyl group), such as 2-phenylethyl, t-butylbenzyl or benzyl, (iii) monomers possessing ethylenic unsaturation(s) comprising at least one carboxylic acid, phosphoric acid, sulfonic acid or anhydride functional group, such as, for example, acrylic acid, methacrylic acid, crotonic acid, maleic anhydride, itaconic acid, fumaric acid, maleic acid, styrenesulfonic acid, vinylbenzoic acid, vinylphosphoric acid, acrylamidopropanesulfonic acid and the salts of these;

(iv) vinyl ethers of formula $R_6$O—CH=$CH_2$ or vinyl esters of formula $R_6$—COO—CH=$CH_2$
in which $R_6$ represents a linear or branched alkyl group comprising from 1 to 22 atoms or a cyclic alkyl group comprising from 3 to 6 carbon atoms and/or an aromatic group, for example of benzene, anthracene and naphthalene type;

(v) vinyl compounds of formula $CH_2$=CH—$R_9$, $CH_2$=CH—$CH_2$—$R_9$ or $CH_2$=C($CH_3$)—$CH_2$—$R_9$
in which $R_9$ is a hydroxyl group, a halogen group (Cl or F), an $NH_2$ group, an $OR_{10}$ group, where $R_{10}$ represents a phenyl group or a $C_1$ to $C_{12}$ alkyl group (the monomer is a vinyl or allyl ether), an acetamide group ($NHCOCH_3$), an $OCOR_{11}$ group, where $R_{11}$ represents a linear or branched alkyl group of 2 to 12 carbons (the monomer is a vinyl or allyl ester), or a group chosen from:
  a linear or branched alkyl group of 1 to 18 carbon atoms in which is(are) optionally inserted one or more heteroatoms chosen from O, N, S and P, said alkyl group additionally being able to be optionally substituted by one or more substituents chosen from hydroxyl groups, halogen atoms (Cl, Br, I and F) and Si($R_4R_5$) groups, where $R_4$ and $R_6$, which are identical or different, represent a $C_1$ to $C_6$ alkyl group or a phenyl group;
  a $C_3$ to $C_{12}$ cycloalkyl group, such as isobornyl or cyclohexyl,
  a $C_3$ to $C_{20}$ aryl group, such as phenyl,
  a $C_4$ to $C_{30}$ aralkyl group ($C_1$ to $C_8$ alkyl group), such as 2-phenylethyl or benzyl,
  a 4- to 12-membered heterocyclic group comprising one or more heteroatoms chosen from O, N and S, the ring being aromatic or nonaromatic,
  a heterocycloalkyl group (alkyl of 1 to 4 carbon atoms), such as furfurylmethyl or tetrahydrofur-furylmethyl, (vi) styrene and its derivatives, in particular such as methylstyrene, chlorostyrene or chloromethylstyrene;

(vii) monomers possessing ethylenic unsaturation comprising one or more silicon atoms, such as methacryloyloxypropyltrimethoxysilane or methacryloyl-oxypropyltris(trimethylsiloxy)silane;

and their salts and their mixtures.

Mention may very particularly be made, among these additional monomers, of methyl(meth)acrylates, n-propyl (meth)acrylates, isopropyl(meth)acrylates, n-butyl(meth) acrylates, t-butyl(meth)acrylates, cyclohexyl(meth)acrylates, methoxyethyl(meth)acrylates, ethoxyethyl(meth) acrylates, trifluoroethyl(meth)acrylates, dimethylaminoethyl (meth)acrylates, diethylaminoethyl(meth)acrylates, 2-hydroxypropyl(meth)acrylates and 2-hydroxyethyl(meth) acrylates, acrylic acid, methacrylic acid, (meth)acrylamide, methacryloyloxypropyltrimethoxysilane, methacryloyloxypropyltris(trimethylsiloxy)-silane, and their salts and their mixtures.

Use may also be made, as additional monomers, of carbon-based or silicone macromonomers having at least one polymerizable end group. The macromonomer is any polymer, in particular oligomer, comprising, on just one of its ends, an end group, in particular a polymerizable end group, capable of reacting during the polymerization reaction with the monomers under consideration to form the side chains of the polymer; said end group can advantageously be a group possessing ethylenic unsaturation capable of polymerizing by the radical route with the monomers constituting the backbone. Said macromonomer makes it possible to form the side chains of the copolymer. The polymerizable group of the macromonomer can advantageously be a group possessing ethylenic unsaturation capable of polymerizing by the radical route. Said polymerizable end group can in particular be a vinyl or (meth)acrylate group. Mention may in particular be made, among the additional macromonomers capable of being employed, of, alone or as a mixture, and their salts:

(i) linear or branched $C_8$-$C_{22}$ alkyl(meth)acrylate homopolymers and copolymers exhibiting a polymerizable end group chosen from vinyl or (meth)acrylate groups, among which may be mentioned poly(2-ethylhexyl acrylate) macromonomers possessing a mono(meth)acrylate end; poly(dodecyl acrylate) or poly(dodecyl methacrylate) macromonomers possessing a mono(meth)-acrylate end; poly(stearyl acrylate) or poly(stearyl methacrylate) macromonomers possessing a mono(meth)-acrylate end. Such macromonomers are disclosed in particular in patents EP 895 467 and EP 96 459.

(ii) polyolefins having an end group possessing ethylenic unsaturation, in particular those having a (meth)acrylate end group. Mention may in particular be made, as examples of such polyolefins, of the following macromonomers, it being understood that they have a (meth)acrylate end group: polyethylene macromonomers, polypropylene macromonomers, polyethylene/polypropylene copolymer macromonomers, polyethylene/polybutylene copolymer macromonomers, polyisobutylene macromonomers, polybutadiene macromonomers, polyisoprene macromonomers, poly(ethylene/butylene)-polyisoprene macromonomers. Such macromonomers are disclosed in particular in U.S. Pat. No. 5,625,005, which mentions ethylene/butylene and ethylene/propylene macromonomers possessing a reactive (meth)acrylate end group. Mention may in particular be made of polyethylene/butylene) methacrylate, such as that sold under the name Kraton Liquid L-1253 by Kraton Polymers.

(iii) polydimethylsiloxanes possessing a mono(meth)-acrylate end group, in particular those of following formula (IIa):

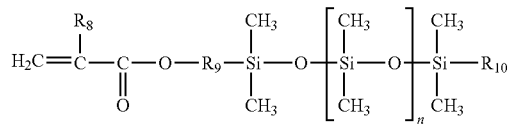

(IIa)

in which:
R$_8$ denotes a hydrogen atom or a methyl group, preferably methyl;
R$_9$ denotes a linear or branched, preferably linear, divalent hydrocarbon group having from 1 to 10 carbon atoms and optionally comprising one or two —O— ether bonds, preferably ethylene, propylene or butylene;
R$_{10}$ denotes a linear or branched alkyl group having from 1 to 10 carbon atoms, in particular from 2 to 8 carbon atoms, preferably methyl, ethyl, propyl, butyl or pentyl;
n denotes an integer ranging from 1 to 300, preferably ranging from 3 to 200 and preferentially ranging from 5 to 100.

Mention may in particular be made, as silicone macromonomers, of monomethacryloyloxypropylpolydimethylsiloxanes, such as those sold under the name PS560-K6 by UCT (United Chemical Technologies Inc.) or under the name MCR-M17 by Gelest Inc.

Mention may be made, among the salts, of those obtained by neutralization of the acid groups using an inorganic base, such as LiOH, NaOH, KOH, Ca(OH)$_2$, NH$_4$OH or Zn(OH)$_2$, or with an organic base, such as a primary, secondary or tertiary alkylamine, in particular triethylamine or butylamine. This primary, secondary or tertiary alkylamine can comprise one or more nitrogen and/or oxygen atoms and can thus comprise, for example, one or more alcohol functional groups; mention may in particular be made of 2-amino-2-methylpropanol, triethanolamine and 2-(dimethylamino)propanol. Mention may also be made of lysine or 3-(dimethylamino)propylamine.

Mention may also be made of salts of inorganic acids, such as sulfuric acid, hydrochloric acid, hydrobromic acid, hydriodic acid, phosphoric acid or boric acid. Mention may also be made of salts of organic acids which can comprise one or more carboxylic acid, sulfonic acid or phosphonic acid groups. These acids can be linear, branched or cyclic aliphatic acids or also aromatic acids. These acids can additionally comprise one or more heteroatoms chosen from O and N, for example in the form of hydroxyl groups. Mention may in particular be made of propionic acid, acetic acid, terephthalic acid, citric acid and tartaric acid.

Preferably, the gradient copolymer according to the invention comprises at least one monomer having a Tg of less than or equal to 20° C., in particular of between −150° C. and 20° C., more particularly of between −130° C. and 18° C. and better still of between −120° C. and 15° C., or a mixture of such monomers.

These monomers can be chosen from the "selected monomers" mentioned above and/or from the additional monomers.

This or these monomers with a Tg≤20° C. can be present in a proportion of 1 to 99% by weight, in particular 10 to 90% by weight, better still 20 to 80% by weight, indeed even 25 to 75% by weight, with respect to the total weight of the copolymer.

Preferably, the copolymer according to the invention thus also comprises at least one monomer having a Tg of greater than or equal to 20° C., in particular of between 25 and 150° C., more particularly of between 30 and 145° C. and better still of between 40 and 140° C., or a mixture of such monomers.

This or these monomers can be chosen from the "selected monomers" mentioned above and/or from the additional monomers.

The monomer or monomers with a Tg 20° C. can thus be present in a proportion of 1 to 99% by weight, in particular 10 to 90% by weight, better still 20 to 80% by weight, indeed even 25 to 75% by weight, with respect to the total weight of the copolymer.

By way of information, it should be noted that isobornyl acrylate has a Tg of 94° C., isobornyl methacrylate has a Tg of 110° C. and isobutyl methacrylate has a Tg of 53° C., and are thus said to be of high Tg, of greater than 20° C., whereas isobutyl acrylate has a Tg of −24° C. and 2-ethylhexyl acrylate has a Tg of −50° C., and are thus said to be of low Tg, of less than 20° C.

In the present description, the term "monomer with a Tg" will denote the monomers for which the homopolymer has such a Tg. In the present invention, the Tg (or glass transition temperature) values are theoretical Tg values determined from the theoretical Tg values of the constitutive monomers of each of the blocks, which can be found in a reference manual, such as the Polymer Handbook, 3rd ed., 1989, John Wiley, according to the following relationship, referred to as the "Fox law":

$$\frac{1}{Tg} = \sum_i \left(\frac{\varpi i}{tgi}\right)$$

wi being the fraction by weight of the monomer i in the block under consideration and Tgi being the glass transition temperature of the homopolymer of the monomer i (in degrees Kelvin).

A person skilled in the art will know to choose the monomers and their amounts according to the result desired, basing himself on his general knowledge, in particular on the relative reactivity of each monomer. In particular, he will choose the monomers and their amounts, and the solvent medium, so as to obtain a copolymer which is preferably soluble in said solvent medium.

The gradient copolymers of the invention can be prepared by a person skilled in the art according to the following procedure:

1) A mixture of the various monomers is prepared, optionally in a solvent, preferably in a stirred reactor. A radical polymerization initiator and an agent for controlling the polymerization are added. The mixture is preferably placed under a gas atmosphere which is inert with respect to radical polymerization, such as nitrogen or argon.

The choice may be made, as optional polymerization solvent, of the solvent medium of the composition, which can thus comprise cosmetic solvents and/or oils such as defined below. In particular, the polymerization solvent can be chosen from alkyl acetates, such as butyl acetate or ethyl acetate, aromatic solvents, such as toluene, or alkanes, such as isododecane, heptane or isohexadecane.

2) The mixture is brought with stirring to the desired polymerization temperature. This temperature is preferably chosen within a range from 10° C. to 160° C., preferably from 25° C. to 130° C.

The choice of the polymerization temperature is preferably optimized according to the chemical composition of the mixture of monomers. Thus, monomers having very high propagation kinetic constants and a weaker affinity for the control agent will preferably be polymerized at low temperature.

3) The polymerization medium is optionally modified during the polymerization, before 90% conversion of the starting monomers is achieved, by further addition of one or more monomers, in particular of the starting mixture. This addition can be carried out in various ways, which can range from the sudden addition all at once to the continuous addition over the entire duration of the polymerization.

4) The polymerization is halted when the desired degree of conversion is achieved. The overall composition of the copolymer depends on this conversion. The polymerization is preferably halted after having achieved at least 50% conversion, in particular at least 60%, preferably after having achieved at least 90% conversion.

5) The possible residual monomers can be removed by any known method, such as by evaporation or by addition of an amount of conventional polymerization initiator, such as peroxide or azo derivatives.

It is also possible to carry out a semicontinuous polymerization, for example by introducing all or part of the optional solvent, a portion of the monomers, in particular 1 to 20% by weight of the total weight of monomers, and a portion of the initiator, in particular 1 to 20% by weight of the total weight of initiator, into a reactor and by then heating to the required temperature. The remainder of the solvent, of the monomers and of the initiator can be introduced by running in during polymerization. They can be introduced by running in separately or identically.

The agent for controlling the polymerization can be (i) a nitroxide or an alkoxyamine; (ii) an organo-metallic complex in the presence of a halogenated compound; or (iii) sulfur derivatives of xanthate, dithioester, trithiocarbonate or carbamate type.

The radical polymerization initiator can be chosen from any conventional polymerization initiator, such as compounds of azo type, and in particular azobisiso-butyronitrile, or of peroxide type, such as organic peroxides having 6 to 30 carbon atoms, in particular benzoyl peroxide.

The radical polymerization initiator can also be an alkoxyamine which can advantageously be chosen to initiate the polymerization and, at the same time, to release the nitroxide controlling this polymerization. The polymerization initiator can be a halogenated organic compound, in particular a halogenated alkyl or ester, such as ethyl 2-bromoisobutyrate.

A person skilled in the art will know to choose the polymerization initiator according to the controlled radical polymerization technique envisaged and/or according to the requirements of the application. Thus, a monofunctional initiator will result in asymmetric chains, whereas a polyfunctional initiator will result in macromolecules having a symmetry starting from a core.

The copolymers according to the invention are very particularly soluble in lipophilic solvent media, such as the solvents, in particular lipophilic solvents, and/or carbon-based oils conventionally employed in cosmetics.

It should be remembered that the term "soluble" is understood to mean that the polymer does not form a precipitate in the solvent. Advantageously, the copolymer according to the invention is soluble at a concentration of at least 1% by weight in isododecane at 25° C., 1 atm., preferably at a concentration of at least 5% by weight, indeed even of at least 10% by weight.

The gradient copolymers according to the invention can be present in the topical cosmetic or dermatological compositions in an amount of 0.1 to 95% by weight, preferably 0.5 to 90% by weight, in particular 1 to 80% by weight, indeed even 5 to 70% by weight, with respect to the total weight of the composition.

The copolymers can thus be present in the composition in the dissolved form, for example dissolved in a cosmetic organic solvent or a cosmetic carbon-based oil.

It has been found that the gradient copolymers according to the invention are very particularly soluble and that they can additionally be dissolved in large amounts without influencing the viscosity of the solution.

The cosmetic or dermatological compositions according to the invention comprise, in addition to said copolymers, a physiologically acceptable medium, in particular a cosmetically or dermatologically acceptable medium, that is to say a medium compatible with keratinous substances, such as the skin of the face or body, the lips, the hair, the eyelashes, the eyebrows and the nails.

The composition can advantageously comprise a solvent medium which can be a fatty phase which can itself comprise oils and/or solvents, preferably lipophilic solvents, and fatty substances which are solid at ambient temperature, such as waxes, pasty fatty substances, gums and their mixtures.

Mention may preferably be made, among the constituents of the fatty phase, of the oils and/or solvents having an overall solubility parameter according to the Hansen solubility space of less than or equal to 20 $(MPa)^{1/2}$, preferably of less than or equal to 18 $(MPa)^{1/2}$, better still of less than or equal to 17 $(MPa)^{1/2}$.

The overall solubility parameter δ according to the Hansen solubility space is defined in the article "Solubility Parameter Values" by Eric A. Grulke in the work "Polymer Handbook", 3rd edition, Chapter VII, pp. 519-559, by the relationship:

$$\delta=(dD^2+dP^2+dH^2)^{1/2}$$

in which
- dD characterizes the London dispersion forces resulting from the formation of dipoles induced during molecular impacts,
- dP characterizes the forces of Debye interactions between permanent dipoles, and
- dH characterizes the forces of specific interactions (hydrogen bond, acid/base or donor/acceptor type, and the like).

The definition of the solvents in the solubility space according to Hansen is described in the paper by C. M. Hansen, "The Three-Dimensional Solubility Parameters", J. Paint Technol., 39, 105 (1967).

Mention may be made, among the oils and/or solvents having an overall solubility parameter according to the Hansen solubility space of less than or equal to 20 $(MPa)^{1/2}$, of volatile or nonvolatile oils which can be chosen from optionally branched, carbon-based, hydrocarbon or fluorinated, natural or synthetic oils, alone or as a mixture; ethers and esters having more than 6 carbon atoms, in particular 6 to 30 carbon atoms; ketones having more than 6 carbon atoms, in particular 6 to 30 carbon atoms; aliphatic fatty monoalcohols having 6 to 30 carbon atoms, the hydrocarbon chain not comprising a substituent group.

The term "nonvolatile oil" is understood to mean an oil capable of remaining on the skin at ambient temperature and atmospheric pressure for at least one hour and having in particular a nonzero vapor pressure at ambient temperature (25° C.) and atmospheric pressure of less than 0.01 mmHg (1.33 Pa).

Mention may in particular be made of nonvolatile carbon-based oils, in particular hydrocarbon oils, of vegetable, mineral, animal or synthetic origin, such as liquid paraffin (or liquid petrolatum), squalane, hydrogenated polyisobutylene (Parleam oil), perhydro-squalene, mink oil, macadamia nut oil, turtle oil, soybean oil, sweet almond oil, calophyllum oil, palm oil, grape seed oil, sesame oil, corn oil, arara oil, rapeseed oil, sunflower oil, cottonseed oil, apricot oil, castor oil, avocado oil, jojoba oil, olive oil, cereal germ oil or Shea butter; linear, branched or cyclic esters having more than 6 carbon atoms, in particular 6 to 30 carbon atoms, such as esters of lanolic acid, of oleic acid, of lauric acid or of stearic acid; esters derived from long-chain acids or alcohols (that is to say, having from 6 to 20 carbon atoms), in particular esters of formula RCOOR' in which R represents the residue of a higher fatty acid comprising from 7 to 19 carbon atoms and R' represents a hydrocarbon chain comprising from 3 to 20 carbon atoms, in particular $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyl-decyl palmitate, 2-octyldodecyl myristate or lactate, di(2-ethylhexyl) succinate, diisostearyl malate, glyceryl triisostearate or diglyceryl triisostearate; higher fatty acids, in particular $C_{14}$-$C_{22}$ fatty acids, such as myristic acid, palmitic acid, stearic acid, behenic acid, oleic acid, linoleic acid, linolenic acid or isostearic acid; higher fatty alcohols, in particular $C_{16}$-$C_{22}$ fatty alcohols, such as ketanol, oleyl alcohol, linoleyl alcohol, linolenyl alcohol, isostearyl alcohol, or octyldodecanol; and their mixtures.

Mention may also be made of decanol, dodecanol, octadecanol, liquid triglycerides of fatty acids of 4 to 10 carbon atoms, such as triglycerides of heptanoic or octanoic acids or triglycerides of caprylic/capric acids; linear or branched hydrocarbons of mineral or synthetic origin, such as liquid paraffins and their derivatives, liquid petrolatum, polydecenes, hydrogenated polyisobutene, such as Parleam; synthetic esters and ethers, in particular of fatty acids, such as, for example, Purcellin oil, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate, heptanoates, octanoates, decanoates of fatty alcohols; polyol esters, such as propylene glycol dioctanoate, neopentyl glycol diheptanoate or diethylene glycol diiso-nonanoate; pentaerythritol esters; fatty alcohols having from 12 to 26 carbon atoms, such as octyldodecanol, 2-butyloctanol, 2-hexyldecanol or 2-undecylpentadecanol.

Mention may also be made of ketones which are liquid at ambient temperature, such as methyl ethyl ketone, methyl isobutyl ketone, diisobutyl ketone, isophorone, cyclohexanone or acetone; propylene glycol ethers which are liquid at ambient temperature, such as propylene glycol monomethyl ether, propylene glycol monomethyl ether acetate or dipropylene glycol mono(n-butyl) ether; short-chain esters (having a total of 3 to 8 carbon atoms), such as ethyl acetate, methyl acetate, propyl acetate, n-butyl acetate or isopentyl acetate; ethers which are liquid at ambient temperature, such as diethyl ether, dimethyl ether or dichlorodiethyl ether; alkanes which are liquid at ambient temperature, such as decane, heptane, dodecane, isododecane, isohexa-decane or cyclohexane; aromatic cyclic compounds which are liquid at ambient temperature, such as toluene and xylene; aldehydes which are liquid at ambient temperature, such as benzaldehyde or acetaldehyde, and their mixtures.

Mention may be made, among volatile compounds, of volatile non-silicone oils, in particular $C_8$-$C_{16}$ isoparaffins, such as isododecane, isodecane, isohexa-decane and, for example, the oils sold under the Isopar and Permethyl trade names, in particular isododecane (Permethyl 99A).

More preferably, mention may be made of volatile or nonvolatile alkanes which are liquid at ambient temperature and more particularly decane, heptane, dodecane, isododecane, isohexadecane, cyclohexane, isodecane and their mixtures.

These oils and/or solvents can generally be present in a content ranging from 0.01 to 95%, preferably from 0.1 to 90%, more preferably from 10 to 85% by weight, with respect to the total weight of the composition, and better still from 30 to 80%.

The composition can additionally comprise a hydrophilic medium comprising water or a mixture of water and of hydrophilic organic solvent(s), such as alcohols and in particular linear or branched lower monoalcohols having from 2 to 5 carbon atoms, such as ethanol, isopropanol or n-propanol, and polyols, such as glycerol, diglycerol, propylene glycol, sorbitol, pentylene glycol and polyethylene glycols, or else hydrophilic $C_2$ ethers and hydrophilic $C_2$-$C_4$ aldehydes.

The water or the mixture of water and of hydrophilic organic solvents can be present in the composition according to the invention in a content ranging from 0.1 to 80% by weight, with respect to the total weight of the composition, and preferably from 1 to 70% by weight.

The composition according to the invention can also comprise waxes and/or gums.

The term "wax" is understood to mean, within the meaning of the present invention, a lipophilic compound which is solid at ambient temperature (25° C.), which has a reversible solid/liquid change in state and which has a melting point of greater than or equal to 30° C. which can range up to 120° C. On bringing the wax to the liquid state (melting), it is possible to render it miscible with the oils which may be present and to form a microscopically homogeneous mixture but, on bringing the temperature of the mixture back to ambient temperature, recrystallization of the wax in the oils of the mixture is obtained. The melting point of the wax can be measured using a differential scanning calorimeter (DSC), for example the calorimeter sold under the name DSC 30 by Metler.

The waxes can be hydrocarbon, fluorinated and/or silicone waxes and can be of vegetable, mineral, animal and/or synthetic origin. In particular, the waxes exhibit a melting point of greater than 25° C. and better still of greater than 45° C. Mention may be made, as waxes which can be used in the composition of the invention, of beeswax, carnauba wax, candelilla wax, paraffin wax, microcrystalline waxes, ceresin or ozokerite; synthetic waxes, such as polyethylene or Fischer-Tropsch waxes, silicone waxes, such as alkyl or alkoxy dimethicones having from 16 to 45 carbon atoms.

The gums are generally polydimethylsiloxanes (PDMS) of high molecular weight or cellulose gums or polysaccharides and the pasty substances are generally hydrocarbon compounds, such as lanolins and their derivatives or also PDMSs.

The nature and the amount of the solid substances depend on the mechanical properties and textures desired. By way of indication, the composition can comprise from 0.01 to 50% by weight of waxes, with respect to the total weight of the composition, and better still from 1 to 30% by weight.

The composition according to the invention can additionally comprise one or more coloring materials chosen from water-soluble dyes, fat-soluble dyes and pulverulent coloring materials, such as pigments, pearlescent agents and glitters well known to a person skilled in the art. The coloring materials can be present in the composition in a content ranging from 0.01 to 50% by weight, with respect to the weight of the composition, preferably from 0.01 to 30% by weight. The term "pigments" should be understood as meaning white or colored and inorganic or organic particles of any shape which are insoluble in the physiological medium and which are intended to color the composition. The term "pearlescent agents" should be understood as meaning iridescent particles of any shape, in particular produced by certain mollusks in their shells or else synthesized. The pigments can be white or colored and inorganic and/or organic. Mention may be made, among inorganic pigments, of titanium dioxide, optionally surface treated, zirconium or cerium oxides, zinc, iron or chromium oxides (the iron oxides being black, yellow or red), manganese violet, ultramarine blue, chromium hydrate, ferric blue or metal powders, such as aluminum powder or copper powder. Mention may be made, among organic pigments, of carbon black, pigments of D & C type, and lakes based on cochineal carmine of barium, strontium, calcium or aluminum. The pearlescent pigments can be chosen from white pearlescent pigments, such as mica covered with titanium oxide or with bismuth oxychloride, colored pearlescent pigments, such as titanium oxide-coated mica covered with iron oxides, titanium oxide-coated mica covered with in particular ferric blue or with chromium oxide, or titanium oxide-coated mica covered with an organic pigment of the abovementioned type, and pearlescent pigments based on bismuth oxychloride. Mention may be made, among water-soluble dyes, of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll or methylene blue.

The composition according to the invention can additionally comprise one or more fillers, in particular in a content ranging from 0.01% to 50% by weight, with respect to the total weight of the composition, preferably ranging from 0.01% to 30% by weight. The term "fillers" should be understood as meaning colorless or white and inorganic or synthetic particles of any shape which are insoluble in the medium of the composition, whatever the temperature at which the composition is manufactured. These fillers are used in particular to modify the rheology or the texture of the composition. The fillers can be inorganic or organic and of any shape, platelet, spherical or oblong, whatever the crystallographic form (for example sheet, cubic, hexagonal, orthorhombic, and the like). Mention may be made of talc, mica, silica, kaolin, polyamide (Nylon®) powders (Orgasol® from Atochem), poly-β-alanine powders, polyethylene powders, powders formed of tetrafluoroethylene polymers (Teflon®), lauroyllysine, starch, boron nitride, polymeric hollow microspheres, such as those of polyvinylidene/acrylonitrile chloride, for example Expancel® (Nobel Industrie), or of acrylic acid copolymers (Polytrap® from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The composition can furthermore comprise an additional polymer, such as a film-forming polymer. According to the present invention, the term "film-forming polymer" is understood to mean a polymer capable of forming, by itself alone or in the presence of an additional agent which is able to form a film, a continuous film which adheres to a support, in particular to keratinous substances. Mention may be made, among the film-forming polymers capable of being used in the composition of the present invention, of synthetic polymers of radical type or of polycondensate type, polymers of natural origin and their mixtures, in particular acrylic polymers, polyurethanes, polyesters, polyamides, polyureas or cellulose polymers, such as nitrocellulose.

The composition according to the invention can also comprise ingredients commonly used in cosmetics, such as vitamins, thickeners, gelling agents, trace elements, softening agents, sequestering agents, fragrances, basifying or acidifying agents, preservatives, sunscreens, surfactants, antioxidants, agents for combating hair loss, antidandruff agents, propellants, ceramides or their mixtures. Of course, a person skilled in the art will take care to choose this or these optional additional compounds and/or their amounts so that the advantageous properties of the composition according to the invention are not, or not substantially, detrimentally affected by the envisaged condition.

The composition according to the invention can be provided in particular in the form of a suspension, a dispersion, a solution, in particular organic, a gel, an emulsion, in particular oil-in-water (O/W) or water-in-oil (W/O) or multiple (W/O/W or polyol/O/W or O/W/O) emulsion, a cream, a foam, a dispersion of vesicles, in particular of ionic or nonionic lipids, a two-phase or multiphase lotion, a spray, a powder, a paste, in particular a soft paste (in particular a paste having a dynamic viscosity at 25° C. of the order of 0.1 to 40 Pa·s under a shear rate of 200 s$^{-1}$, after measuring for 10 minutes by cone/plate geometry). The composition can be anhydrous; for example, it can be an anhydrous paste.

A person skilled in the art can choose the appropriate formulation form and its method of preparation on the basis of his general knowledge, taking into account, on the one hand, the nature of the constituents used, in particular their solubility in the support, and, on the other hand, the application envisaged for the composition.

The composition according to the invention can be a makeup composition, in particular a product for the complexion, such as a foundation, a face powder or an eyeshadow; a product for the lips, such as a lipstick or a lip care product; a concealer; a blusher, a mascara or an eyeliner; a product for making up the eyebrows, a lip pencil or an eye pencil; a product for the nails, such as a nail varnish or a nail care product; a product for making up the body; a product for making up the hair (hair mascara or lacquer). The composition according to the invention can be a composition for protecting or caring for the skin of the face, of the neck, of the hands or of the body, in particular a composition for combating wrinkles or fatigue which makes it possible to give radiance to the skin, a moisturizing or treating composition; an antisun or artificial tanning composition. The composition according to the invention can also be a hair product, in particular for the form retention of the hairstyle or the shaping of the hair. The hair compositions are preferably shampoos, gels, hairsetting lotions, blow drying lotions or fixing and styling compositions, such as lacquers or sprays. The lotions can be packaged in various forms, in particular in vaporizers, pump-action sprays or aerosol containers, in order to provide for application of the composition in the vaporized form or in the foam form. Such packaging forms are indicated, for example, when it is desired to obtain a spray or a foam for the fixing or the treatment of the hair.

Advantageously, the composition according to the invention can be a makeup composition, in particular a foundation or a lipstick.

Another subject matter of the invention is a cosmetic process for making up or caring for keratinous substances, in particular the skin of the body or face, the nails, the hair and/or the eyelashes, comprising the application, to said substances, of a cosmetic composition as defined above.

In particular, a subject matter of the invention is a cosmetic process for making up the skin of the face and/or the lips, comprising the application, to said substances, of a foundation or lipstick cosmetic composition as defined above.

EXAMPLE 1

3.5 g of isobornyl acrylate ($1.7 \times 10^{-2}$ mol), 3.5 g of isobornyl methacrylate ($1.6 \times 10^{-2}$ mol), 3 g of isobutyl acrylate ($2.3 \times 10^{-2}$ mol) and 10 g of butyl acetate are mixed in a 100 ml three-necked flask equipped with a reflux condenser and placed under an argon flow. This mixture is degassed by bubbling with argon for 15 minutes and then 40 mg of CuBr, 49 mg of PMDETA (N,N,N',N',N''-pentamethyldiethylenetriamine) and 55.6 mg of ethyl 2-bromoisobutyrate are added. The reaction mixture is brought to 100° C. for 2 hours and then filtered through alumina.

A solution of the polymer in butyl acetate (50% of dry matter DM) is obtained.

The butyl acetate can be distilled off and can be substituted by isododecane (10 g). A solution of the polymer in isododecane (50% DM) is then obtained.

EXAMPLE 2

3.5 g of isobornyl acrylate, 3.5 g of isobornyl methacrylate, 3 g of 2-ethylhexyl acrylate and 10 g of butyl acetate are mixed in a 100 ml three-necked flask equipped with a reflux condenser and placed under an argon flow.

This mixture is degassed by bubbling with argon for 15 minutes and then 40 mg of CuBr, 49 mg of PMDETA (N,N,N',N',N''-pentamethyldiethylenetriamine) and 55.6 mg of ethyl 2-bromoisobutyrate are added. The reaction mixture is brought to 100° C. for 2 hours and then filtered through alumina.

A solution of the polymer in butyl acetate (50% of dry matter DM) is obtained.

The butyl acetate can be distilled off and can be substituted by isododecane (10 g). A solution of the polymer in isododecane (50% DM) is then obtained.

EXAMPLE 3

5 g of isobornyl acrylate, 5 g of isobutyl acrylate and 10 g of butyl acetate are mixed in a 100 ml three-necked flask equipped with a reflux condenser and placed under an argon flow.

This mixture is degassed by bubbling with argon for 15 minutes and then 40 mg of CuBr, 49 mg of PMDETA (N,N,N',N',N''-pentamethyldiethylenetriamine) and 55.6 mg of ethyl 2-bromoisobutyrate are added. The reaction mixture is brought to 100° C. for 2 hours and then filtered through alumina.

A solution of the polymer in butyl acetate (50% of dry matter DM) is obtained.

The butyl acetate can be distilled off and can be substituted by isododecane (10 g). A solution of the polymer in isododecane (50% DM) is then obtained.

EXAMPLE 4

A nail varnish is prepared which comprises:
40% by weight of solution of the polymer of example 1 in butyl acetate with a DM of 50%
q.s. for 100% of organic solvents (butyl acetate and ethyl acetate).

EXAMPLE 5

An anhydrous foundation is prepared which comprises (% by weight):

| | |
|---|---|
| Polyethylene wax | 12% |
| Volatile silicone oils | 25% |
| Phenyl trimethicone | 20% |

| | |
|---|---|
| Poly (methyl methacrylate) microspheres | 12% |
| Solution of the polymer of example 2 in isododecane with a DM of 50% (i.e., 6% of polymer dry matter) | 12% |
| Isododecane | q.s. for 100% |

Preparation:

The waxes are melted and then, when all is clear, the phenyl trimethicone is added with stirring and the silicone oils are added; subsequently the microspheres, the isododecane and the polymer are added. The mixture is homogenized for 15 minutes and then the resulting composition is cast and left to cool. An anhydrous foundation is obtained.

EXAMPLE 6

A lipstick stick is prepared which comprises:

| | |
|---|---|
| Polyethylene wax | 15% |
| Solution of the polymer of example 3 in isododecane with a DM of 50% (i.e., 10% of polymer dry matter) | 20% |
| Hydrogenated polyisobutene (Parleam from Nippon Oil Fats) | 25% |
| Pigments | 10% |
| Isododecane | q.s. for 100% |

The composition obtained exhibits good cosmetic properties after application to the lips.

EXAMPLE 7

A foundation composition is prepared which comprises (% by weight):

| Phase A | |
|---|---|
| Cetyl dimethicone copolyol (Abil EM 90 from Goldschmidt) | 3 g |
| Isostearyl diglyceryl succinate (Imwitor 780 K from Condea) | 0.6 g |
| Pigments (oxides of iron and of titanium) | 10 g |
| Polyamide (Nylon 12) powder | 8 g |
| Solution of the polymer of example 1 in isododecane with a DM of 50% (i.e., 8.5% of polymer dry matter) | 17 g |
| Fragrance | q.s. |
| Isododecane | 10 g |

| Phase B | |
|---|---|
| Magnesium sulfate | 0.7 g |
| Preservative | q.s. |
| Water | q.s. for 100 g |

The composition obtained exhibits good cosmetic properties.

What is claimed is:

1. A cosmetic process for making up or caring for keratinous substances which comprises applying to said substances a cosmetic composition comprising, in a physiologically acceptable medium, at least one gradient copolymer comprising at least two different monomers chosen from isobornyl acrylate, isobornyl methacrylate, isobutyl acrylate, isobutyl methacrylate and 2-ethylhexyl acrylate, wherein the copolymer is soluble in isododecane at 25° C., 1 atm., at a concentration of at least 1% by weight.

2. The cosmetic process according to claim 1, wherein the keratinous substances are chosen from the skin of the body or face, the nails, the hair and the eyelashes.

3. The cosmetic process according to claim 1, wherein a first monomer chosen from isobornyl acrylate, isobornyl methacrylate, isobutyl acrylate, isobutyl methacrylate and 2-ethylhexyl acrylate is present in an amount ranging from 1 to 99% by weight, relative to the weight of the final copolymer.

4. The cosmetic process according to claim 3, wherein said first monomer is present in an amount ranging from 30 to 70% by weight, relative to the weight of the final copolymer.

5. The cosmetic process according to claim 3, wherein a second monomer chosen from isobornyl acrylate, isobornyl methacrylate, isobutyl acrylate, isobutyl methacrylate and 2-ethylhexyl acrylate, but different from said first monomer, is present in an amount ranging from 1 to 99% by weight, relative to the weight of the final copolymer.

6. The cosmetic process according to claim 5, wherein said second monomer is present in an amount ranging from 30 to 70% by weight, relative to the weight of the final copolymer.

7. The cosmetic process according to claim 1, wherein said copolymer further comprises a third monomer, chosen from isobornyl acrylate, isobornyl methacrylate, isobutyl acrylate, isobutyl methacrylate and 2-ethylhexyl acrylate, present in an amount ranging from 1 to 50% by weight, relative to the weight of the final copolymer.

8. The cosmetic process according to claim 7, wherein said third monomer is present in an amount ranging from 10 to 35% by weight, relative to the weight of the final copolymer.

9. The cosmetic process according to claim 1, wherein the total amount of monomers chosen from isobornyl acrylate, isobornyl methacrylate, isobutyl acrylate, isobutyl methacrylate and 2-ethylhexyl acrylate in the final copolymer ranges from 50 to 100% by weight, relative to the weight of the final copolymer.

10. The cosmetic process according to claim 9, wherein the total amount of monomers chosen from isobornyl acrylate, isobornyl methacrylate, isobutyl acrylate, isobutyl methacrylate and 2-ethylhexyl acrylate in the final copolymer is present in an amount ranging from 90 to 95% by weight, relative to the weight of the final copolymer.

11. The cosmetic process according to claim 1, wherein said copolymer comprises at least one of the following combinations of monomers:
  isobornyl acrylate and isobornyl methacrylate;
  isobornyl acrylate and isobutyl acrylate;
  isobornyl acrylate and isobutyl methacrylate;
  isobornyl acrylate and 2-ethylhexyl acrylate;
  isobornyl methacrylate and isobutyl acrylate;
  isobornyl methacrylate and isobutyl methacrylate;
  isobornyl methacrylate and 2-ethylhexyl acrylate;
  isobornyl acrylate, isobornyl methacrylate and 2-ethylhexyl acrylate;
  isobornyl acrylate, isobornyl methacrylate and isobutyl acrylate;
  isobornyl acrylate, isobutyl methacrylate and 2-ethylhexyl acrylate;
  isobornyl acrylate, isobutyl methacrylate and isobutyl acrylate; and
  isobornyl methacrylate, isobutyl methacrylate and isobutyl acrylate.

12. The cosmetic process according to claim 1, wherein said copolymer further comprises at least one additional monomer, other than those chosen from isobornyl acrylate, isobornyl methacrylate, isobutyl acrylate, isobutyl methacrylate and 2-ethylhexyl acrylate.

13. The cosmetic process according to claim 12, wherein the at least one additional monomer is present in an amount ranging from 0 to 50% by weight, relative to the weight of the final copolymer.

14. The cosmetic process according to claim 13, wherein the at least one additional monomer is present in an amount ranging from 5 to 10% by weight, with respect to the weight of the final copolymer.

15. The cosmetic process according to claim 12, wherein the at least one additional monomer is chosen, alone or as a mixture, from:
(i) (meth)acrylates of formula $CH_2=CHCOOR$ or $CH_2=C(CH_3)COOR$ wherein R is chosen from:
a linear or branched alkyl group comprising 1 to 30 carbon atoms in which is optionally inserted at least one heteroatom chosen from O, N, S and P, said alkyl groups being optionally substituted by at least one substituent chosen from —OH, halogen atoms chosen from Cl, Br, I, and F, —$NR_4R_5$ groups, wherein $R_4$ and $R_5$, which are identical or different, are each independently chosen from hydrogen atoms, linear or branched $C_1$ to $C_6$ alkyl groups, phenyl groups; and polyoxyalkylene groups composed of the repetition of 5 to 30 oxyalkylene units;
a $C_3$ to $C_{12}$ cycloalkyl group, said cycloalkyl group optionally comprising, in its chain, at least one heteroatom chosen from O, N, S and P and being optionally substituted by at least one substituent chosen from —OH and halogen atoms chosen from Cl, Br, I, and F;
a $C_4$ to $C_{20}$ aryl group or a $C_5$ to $C_{30}$ aralkyl group wherein the alkyl portion is a $C_1$ to $C_8$ alkyl;
(ii) (meth)acrylamides of formula $CH_2=CHCONR_4R_5$ or $CH_2=C(CH_3) CONR_4R_5$ wherein $R_4$ and $R_5$, which are identical or different, are each independently chosen from hydrogen atoms and:
a) linear or branched alkyl groups comprising from 1 to 18 carbon atoms in which is optionally inserted at least one heteroatom chosen from O, N, S and P; said alkyl group being optionally substituted by at least one substituent chosen from hydroxyl groups, halogen atoms chosen from Cl, Br, I, and F and $Si(R_4R_5)$ groups, wherein $R_4$ and $R_5$, which are identical or different, are each independently chosen from $C_1$ to $C_6$ alkyl groups and phenyl groups;
b) $C_3$ to $C_{12}$ cycloalkyl groups, and heterocycloalkyl groups having an alkyl portion of 1 to 4 carbon atoms,
c) $C_4$ to $C_{20}$ aryl groups,
d) $C_5$ to $C_{30}$ aralkyl groups, wherein said alkyl portion has $C_1$ to $C_8$ alkyl groups,
(iii) monomers possessing at least one ethylenic unsaturation comprising at least one functional group chosen from carboxylic acids, phosphoric acids, sulfonic acids, and anhydrides, and the salts thereof;
(iv) vinyl ethers of formula $R_6O—CH=CH_2$ and vinyl esters of formula $R_6—COO—CH=CH_2$
wherein $R_6$ is chosen from a linear or branched alkyl group comprising from 1 to 22 atoms, a cyclic alkyl group comprising from 3 to 6 carbon atoms, and an aromatic group;
(v) vinyl compounds of formula $CH_2=CH—R_9$, $CH_2=CH—CH_2—R_9$ or $CH_2=C(CH_3)—CH_2—R_9$ wherein $R_9$ is chosen from a hydroxyl group, a halogen group chosen from Cl and F, an $NH_2$ group, an $OR_{10}$ group, wherein $R_{10}$ is chosen from a phenyl group and a $C_1$ to $C_{12}$ alkyl group such that the monomer is a vinyl or allyl ether, an acetamide group ($NHCOCH_3$), an $OCOR_{11}$ group, wherein $R_{11}$ is a linear or branched alkyl group of 2 to 12 carbons such that the monomer is a vinyl or allyl ester, and a group chosen from:
a linear or branched alkyl group of 1 to 18 carbon atoms in which is optionally inserted at least one heteroatom chosen from O, N, S and P, said alkyl group additionally being optionally substituted by at least one substituent chosen from hydroxyl groups, halogen atoms chosen from Cl, Br, I, and F and $Si(R_4R_5)$ groups, wherein $R_4$ and $R_5$, which are identical or different, are each independently chosen from $C_1$ to $C_6$ alkyl groups and phenyl groups;
a $C_3$ to $C_{12}$ cycloalkyl group,
a $C_3$ to $C_{20}$ aryl group,
a $C_4$ to $C_{30}$ aralkyl group ($C_1$ to $C_8$ alkyl groups),
a 4- to 12-membered heterocyclic group comprising at least one heteroatom chosen from O, N and S, the ring being aromatic or nonaromatic,
a heterocycloalkyl group wherein said alkyl portion comprises 1 to 4 carbon atoms,
(vi) styrene and its derivatives;
(vii) monomers possessing ethylenic unsaturation comprising at least one silicon atom;
and salts and mixtures thereof;
with the proviso that the at least one additional monomer is not chosen from isobornyl acrylate, isobornyl methacrylate, isobutyl acrylate, isobutyl methacrylate and 2-ethylhexyl acrylate.

16. The cosmetic process according to claim 12, wherein the at least one additional monomer is chosen from methyl (meth)acrylates, n-propyl (meth)acrylates, isopropyl (meth)acrylates, n-butyl (meth)acrylates, t-butyl (meth)acrylates, cyclohexyl (meth)acrylates, methoxyethyl (meth)acrylates, ethoxyethyl (meth)acrylates, trifluoroethyl (meth)acrylates, dimethylaminoethyl (meth)acrylates, diethylaminoethyl (meth)acrylates, 2-hydroxypropyl (meth)acrylates, 2-hydroxyethyl (meth)acrylates, acrylic acid, methacrylic acid, (meth) acrylamide, methacryloyloxy-propyltrimethoxysilane, and methacryloyloxypropyltris(trimethylsiloxy)silane, and salts and mixtures thereof.

17. The cosmetic process according to claim 12, wherein the at least one additional monomer is chosen, alone or as a mixture, from carbon-based or silicone macro-monomers having at least one polymerizable end group and their salts.

18. The cosmetic process according to claim 17, wherein said carbon-based or silicone macro-monomers having at least one polymerizable end group, and salts thereof, are chosen from
(i) linear or branched $C_8$-$C_{22}$ alkyl (meth)acrylate homopolymers and copolymers comprising a polymerizable end group chosen from vinyl and (meth)acrylate groups;
(ii) polyolefins comprising an end group having ethylenic unsaturation; and
(iii) polydimethylsiloxanes comprising a mono(meth)acrylate end group.

19. The cosmetic process according to claim 1, wherein the copolymer is soluble in isododecane at 25° C., 1 atm., at a concentration of at least 10% by weight.

20. The cosmetic process according to claim 1, wherein the copolymer has a weight polydispersity index of less than or equal to 3.

21. The cosmetic process according to claim 20, wherein the copolymer has a weight polydispersity index ranging from 1.2 to 1.8.

22. The cosmetic process according to claim 1, wherein the copolymer is present in an amount ranging from 0.1 to 95% by weight, relative to the total weight of the composition.

23. The cosmetic process according to claim 1, wherein the copolymer is present in an amount ranging from 5 to 70% by weight, relative to the total weight of the composition.

24. The cosmetic process according to claim 1, wherein said composition comprises at least one oil and/or solvent chosen from volatile or nonvolatile oils which can be chosen from optionally branched, carbon-based, hydrocarbon or fluorinated, natural or synthetic oils, alone or as a mixture; ethers and esters having more than 6 carbon atoms; ketones having more than 6 carbon atoms; aliphatic fatty monoalcohols having 6 to 30 carbon atoms, wherein the hydrocarbon chain does not comprise a substituent group.

25. The cosmetic process according to claim 24, wherein the at least one oil and/or solvent is chosen from volatile or nonvolatile alkanes chosen from decane, heptane, dodecane, isododecane, isohexa-decane, cyclohexane and mixtures thereof.

26. The cosmetic process according to claim 1, wherein said composition comprises at least from 0.01 to 95% by weight of at least one oil and/or solvent, relative to the total weight of the composition.

27. The cosmetic process according to claim 1, wherein said composition comprises at least from 30 to 80% by weight of at least one oil and/or solvent, relative to the total weight of the composition.

28. The cosmetic process according to claim 1, wherein said composition further comprises a constituent chosen from a hydrophilic medium comprising water or a mixture of water and of hydrophilic organic solvent; waxes; gums; coloring materials; fillers; polymers; vitamins, thickeners, gelling agents, trace elements, softening agents, sequestering agents, fragrances, basifying or acidifying agents, preservatives, sunscreens, surfactants, antioxidants, agents for combating hair loss, antidandruff agents, propellants, ceramides and mixtures thereof.

29. The cosmetic process according to claim 1, wherein the composition is in a form chosen from a suspension, a dispersion, a solution a gel, an emulsion, a cream, a foam, a dispersion of vesicles, a two-phase or multiphase lotion, a spray, a powder, a paste and in the anhydrous form, for example of an anhydrous paste.

30. The cosmetic process according to claim 29, wherein the composition is in a form chosen from an organic solution; oil-in-water (O/W), water-in-oil (W/O), or a multiple (W/O/W or polyol/O/W or O/W/O) emulsion, a cream, a foam, a dispersion of vesicles comprising ionic or nonionic lipids; a soft paste; and an anhydrous paste.

31. The cosmetic process according to claim 1, wherein the composition is chosen from a makeup composition; a product for the lips; a concealer; a blusher, a mascara, an eyeliner; a product for making up the eyebrows, a lip pencil, an eye pencil; a product for the nails; a product for making up the body; a product for making up the hair; a composition for protecting or caring for the skin of the face, of the neck, of the hands or of the body; an antisun or artificial tanning composition; and a hair composition.

32. The cosmetic process according to claim 30, wherein the composition is chosen from a foundation, a face powder or an eye shadow.

33. The cosmetic process according to claim 31, wherein the composition is in the form chosen from a foundation, a face powder, an eyeshadow, a lipstick, a lip care product, a nail varnish, a nail care product, hair mascara, hair lacquer, a composition for combating wrinkles or fatigue, a moisturizing composition, a treating composition and a hair composition, form the form retention of the hairstyle or the shaping of the hair.

34. The cosmetic process according to claim 1, wherein said first monomer is isobornyl acrylate and is present in an amount ranging from comprising from 30 to 70% by weight, relative to the weight of the final copolymer and wherein said second monomer is isobornyl methacrylate and is present in an amount ranging from comprising from 30 to 70% by weight, relative to the weight of the final copolymer; and wherein the total amount of monomers isobornyl acrylate and isobornyl methacrylate in the final copolymer ranges from 50 to 100% by weight, relative to the weight of the final copolymer.

35. The cosmetic process according to claim 33, which further comprises isobutyl acrylate as a third monomer in an amount of 10 to 35% by weight, relative to the weight of the final copolymer.

36. The cosmetic process according to claim 33, which further comprises 2-ethylhexyl acrylate as a third monomer in an amount of 10 to 35% by weight, relative to the weight of the final copolymer.

* * * * *